(12) United States Patent
Tutak

(10) Patent No.: US 9,775,694 B2
(45) Date of Patent: Oct. 3, 2017

(54) MATERIAL DEPOSITION DEVICE AND METHOD OF USE

(71) Applicant: ADA FOUNDATION, Chicago, IL (US)

(72) Inventor: Wojtek Tutak, Frederick, MD (US)

(73) Assignee: American Dental Association Foundation, Chicago, IL (US)

(*) Notice: Subject to any disclaimer, the term of this patent is extended or adjusted under 35 U.S.C. 154(b) by 243 days.

(21) Appl. No.: 14/561,978

(22) Filed: Dec. 5, 2014

(65) Prior Publication Data
US 2016/0157978 A1    Jun. 9, 2016

(51) Int. Cl.
| | | |
|---|---|---|
| A61C 19/06 | (2006.01) |
| B05B 7/06 | (2006.01) |
| B05B 7/16 | (2006.01) |
| D01D 4/02 | (2006.01) |
| D01D 5/14 | (2006.01) |
| A61L 27/18 | (2006.01) |
| A61L 27/22 | (2006.01) |

(52) U.S. Cl.
CPC ............ *A61C 19/06* (2013.01); *A61C 19/063* (2013.01); *A61L 27/18* (2013.01); *A61L 27/222* (2013.01); *B05B 7/062* (2013.01); *B05B 7/1606* (2013.01); *D01D 4/025* (2013.01); *D01D 4/027* (2013.01); *D01D 5/14* (2013.01); *A61L 2400/06* (2013.01); *A61L 2430/02* (2013.01); *A61L 2430/12* (2013.01)

(58) Field of Classification Search
CPC ........................................................ D04H 3/02

USPC ........................................................ 264/37.24
See application file for complete search history.

(56) References Cited

U.S. PATENT DOCUMENTS

| | | | |
|---|---|---|---|
| 8,641,960 B1 | 2/2014 | Medeiros et al. | |
| 2005/0056956 A1* | 3/2005 | Zhao ............... | D01D 4/025 264/37.24 |
| 2010/0062529 A1 | 3/2010 | Zimmermann et al. | |
| 2013/0284830 A1 | 10/2013 | Wells et al. | |

FOREIGN PATENT DOCUMENTS

| | | |
|---|---|---|
| EP | 1425105 A1 | 6/2004 |
| WO | 03/015927 A1 | 2/2003 |

OTHER PUBLICATIONS

Tutak et al., "The Support of bone marro stromal cell differenatioation by airbrused nanofiber scaffolds," Biomaterials. Jan. 11, 2013, pp. 2389-2398, vol. 34, Elsevier Ltd. Jan. 11, 2013, http://dx.doi.org/10.1016/j.biomaterials.2012.12.020.

(Continued)

*Primary Examiner* — Dah-Wei D Yuan
*Assistant Examiner* — Andrew Bowman

(57) ABSTRACT

A material deposition device includes a solution supply component, a gas supply component, and a co-axial discharge mechanism. The co-axial discharge mechanism includes a solution discharge mechanism, and a gas discharge mechanism co-axial with the solution discharge mechanism. The material deposition device further includes an alignment component that aligns the solution discharge mechanism in a center of the gas discharge mechanism; and an orifice plate with a number of turbulence inducing structures that induce turbulence in gas exiting the gas discharge mechanism.

10 Claims, 10 Drawing Sheets

(56) References Cited

OTHER PUBLICATIONS

S.P. Lin et al., "Drop and Spray Formation from a Liquid Jet," Annu.Rev.Fluid Mech , 1998, pp. 85-105, vol. 30, Annual Reviews Inc., www.annualreviews.org.

Ribeiro, Clarisse et al., "Influence of Processing Conditions on Polymorphism and Nonfiber Morphology of Electroactive Poly(vinylidene Fluoride) Electrospun Membranes," Soft Materials. Aug. 27, 2010, pp. 274-287, vol. 8:3, Taylor & Francis, DOI: 10.1080/1539445X.2010.495630; www.tandfonlin.com/loi.lsfm20.

Medeiros, Eliton S., "Solution Blow Spinning: A New Method to Produce Micro-and Nonofibers from Polymer Solutions," Journal of Applied Polymer Science, Apr. 27, 2009, pp. 2322-2330, vol. 113, Wiley Periodicals, Inc. DOI: 10.1002/app 30275; www.interscience.wiley.com.

Heo, Younsuk et al. "The scaling of zero-shear viscosities of semidilute polymer solutions with concentration," Journal of Rheology, Sep./Oct. 2005, pp. 1117-1128 vol. 49, The Society of Rheology, http://dx.doi.org/10.1122/1.1993595; www.journalofrheology.org/resource/1/JORHD2/v49/i5.

Bingan Lu et al. "A new ultrahigh-speed method for the preparation of nanofibers containing living cells. A bridge towards industrial bioengineering applications," Nanoscale, Jan. 10, 2012, 10 pages, vol. 4, The Royal Society of Chemistry 2012, http://pubs.rsc.org; www.rsc.org/nanoscale; doi 10.1039/C2NR11430E.

Srinivasan, Siddarth et al., "Solution spraying of poly(methyl methacrylate) blends to fabricate microtextured, superoleophobic surfaces," Polymer, May 14, 2011, pp. 3209-3218. vol. 52, Elsevier Ltd., doi:10.1016/j.polymer.2011.05.008; www.elsevier.com/locate/polymer.

Aly, A. Abou El-Azm, et al. "Experimental Study of the Pressure Drop after Fractal-Shaped Orifices in a Turbulent Flow Pipe," World Academy of Science, Engineering and Technology, Apr. 20, 2008, 4 pages, vol. 2, No. 4, waset.org/Publication/12125.

Guan, Ketian et al., "Fabrication and Properties of Polyurethane Nanofibers Nonwoven by Solution Blowing," 2011, (5 pages), Trans Tech Publications, Switzerland, doi: 10.4028/www.scientific.net/AMR.332-334.1339.

Oliveira, Juliano E. et al, "Structural and Morphological Characterization of Micro and Nonofibers Produced by Electrospinning and Solution Blow Spinning: A Comparative Study," Advances in Materials Science and Engineering, 15 pages (with coversheet), vol. 2013, Article ID 409572, Hindawi Publishing Corporation, http://dx.doi.org/10.1155/2013/409572.

Oliveira, Juliano E. et al., "Nano and Submicrometric Fibers of Poly(D,L-Lactide) Obtained by Solution Blow Spinning: Process and Solution Variables," Jul. 12, 2011, pp. 3396-3405, vol. 122, Wiley Periodicals, Inc DOI: 10.1002/app. 34410; wileyonlinelibrary.com.

* cited by examiner

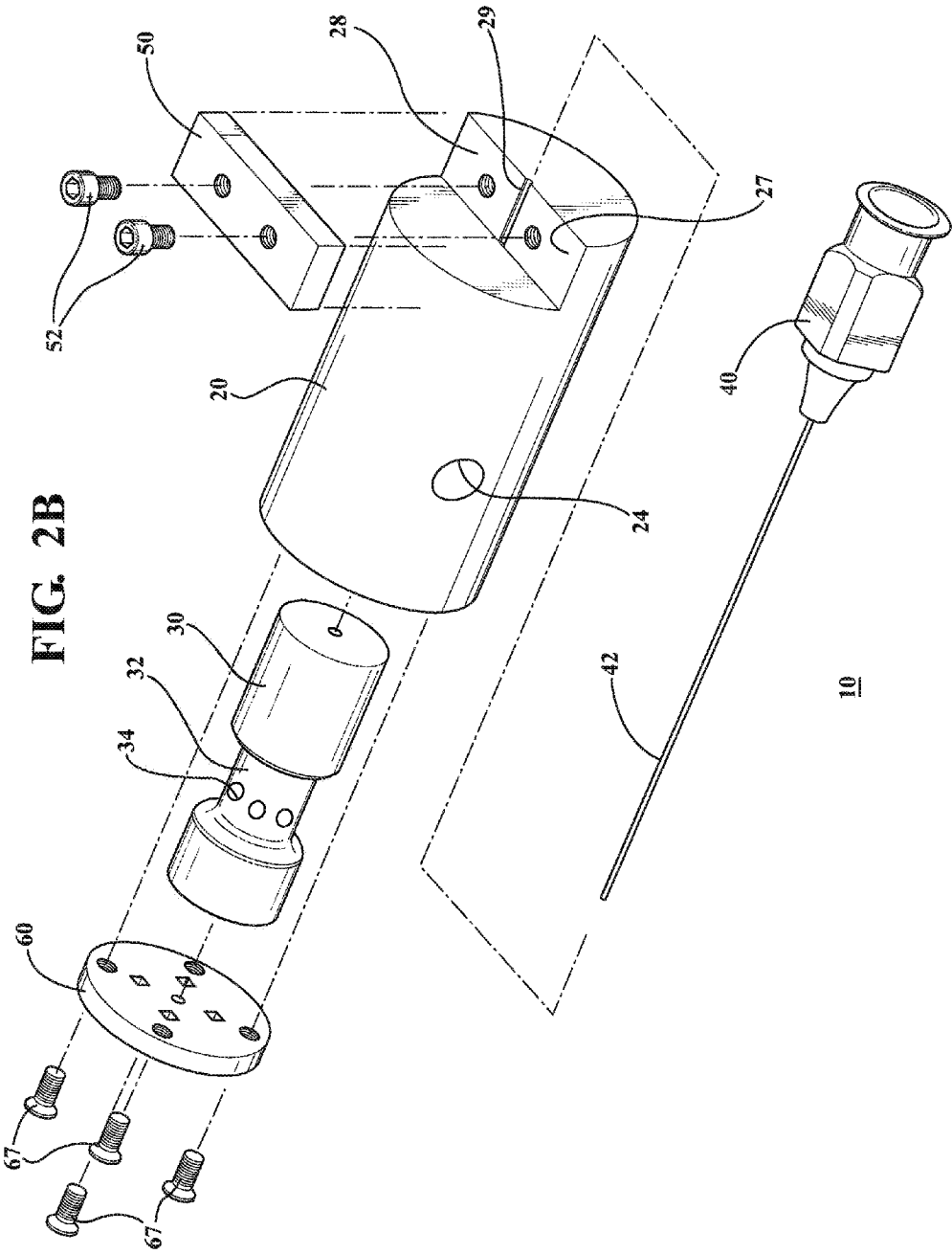

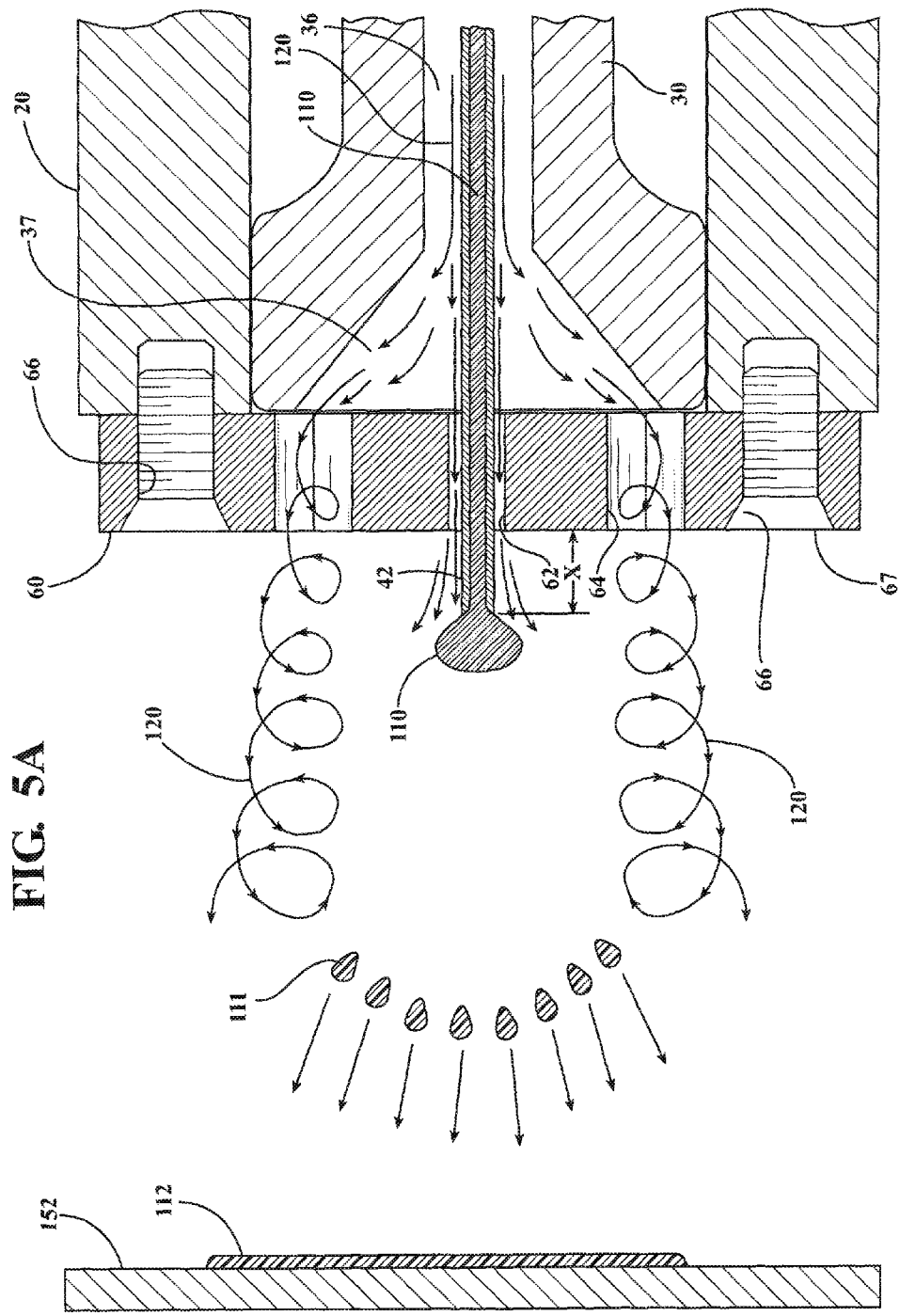

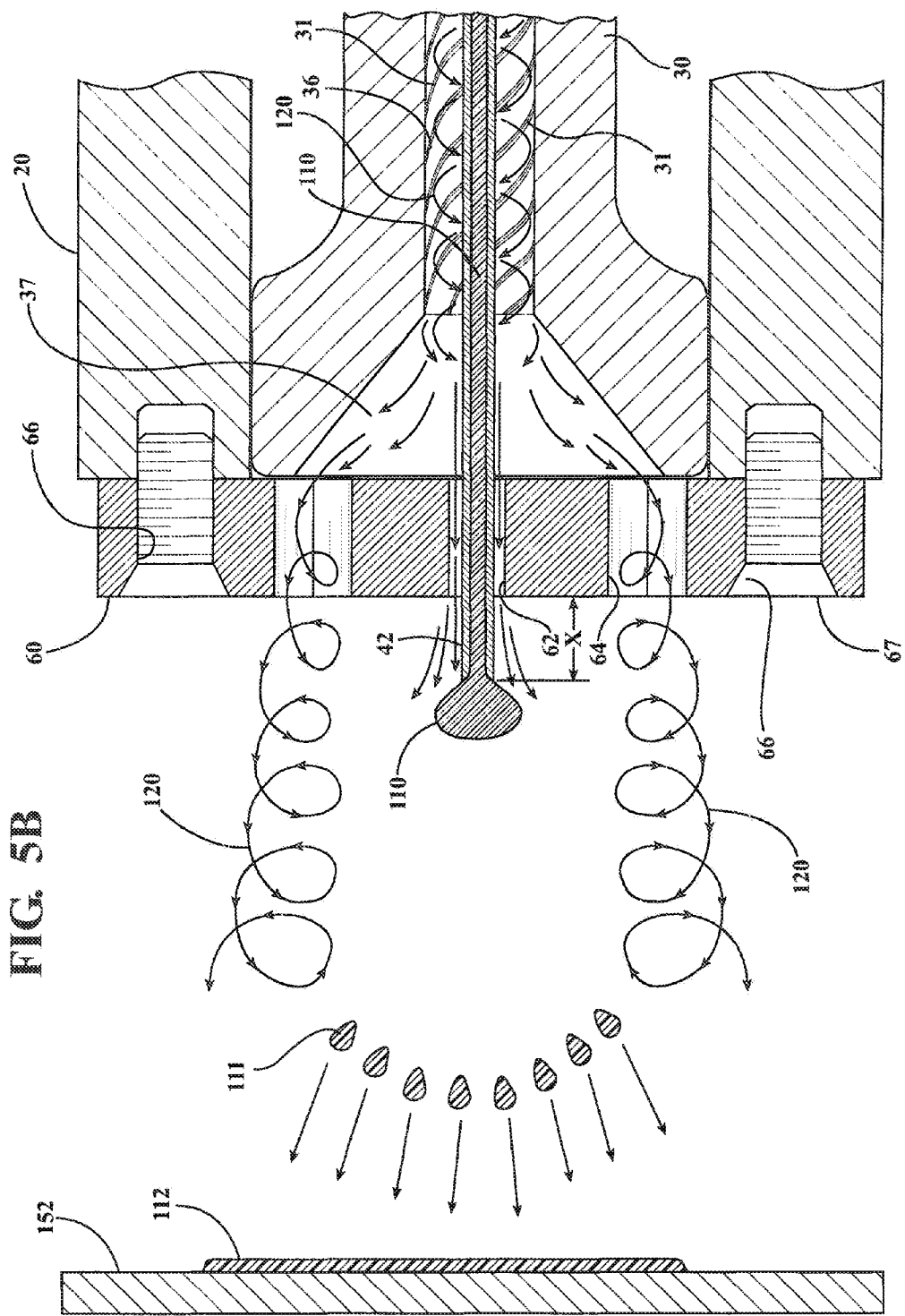

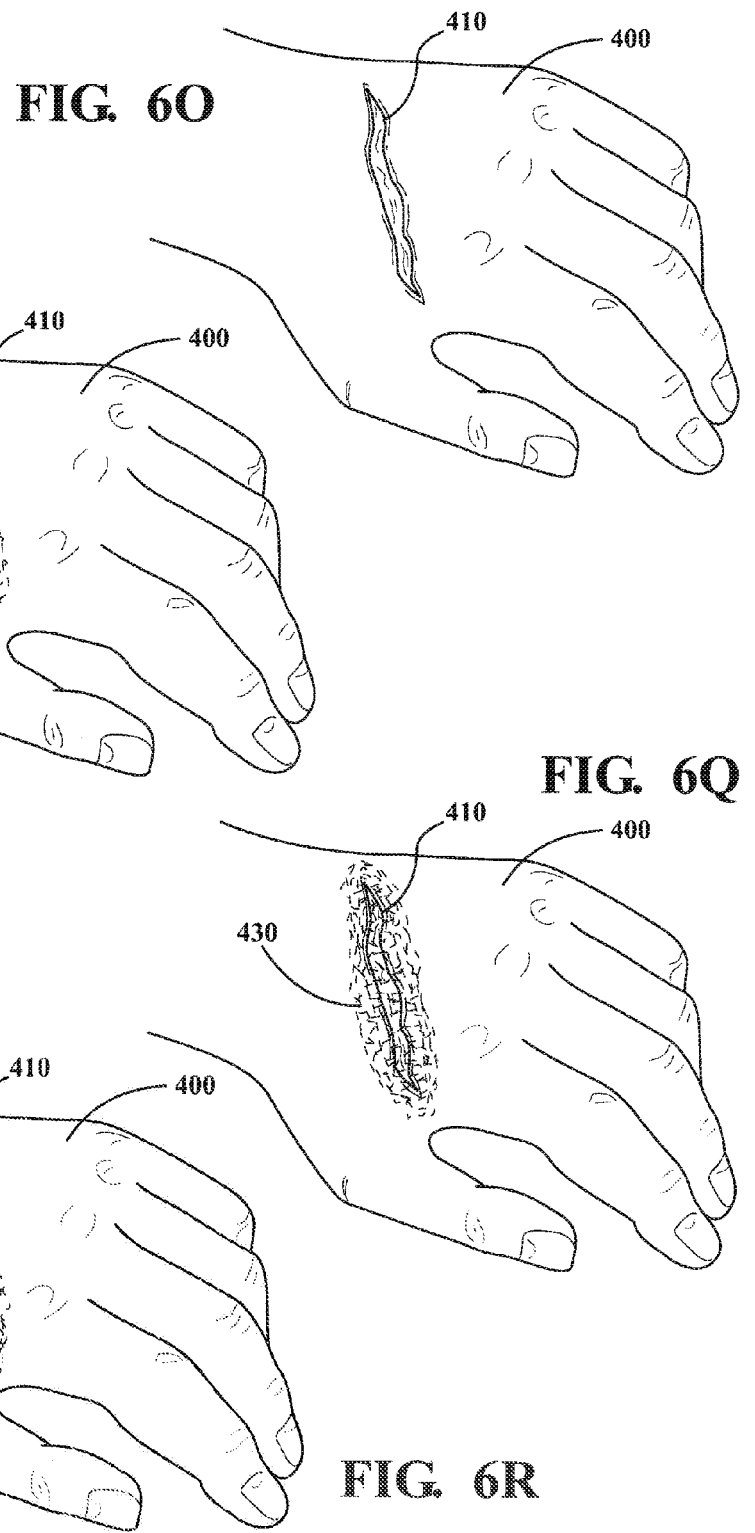

MATERIAL DEPOSITION DEVICE AND METHOD OF USE

BACKGROUND

Devices and methods are known for deposition of biological and non-biological materials in a variety of applications. Some such materials are nanofibers, which may have applications in medicine including artificial organ components, tissue engineering, implant material, drug delivery, wound dressing, and medical textile materials. For example, in wound healing applications, nanofibers, which have a large ratio of surface area to volume (i.e., a high aspect ratio), assemble at an injury site and stay in place thereby providing a close fit for direct and optimum material-tissue interaction, attracting and interacting with surrounding cells, and directing their development so as to lead to tissue regeneration. In addition, the fibers may be used to deliver biomolecules (for example, growth factors) to stimulate surrounding cells.

Nanofibers also may be used as protective materials such as sound absorption materials, protective clothing for use against chemical and biological warfare agents, and sensor applications for detecting chemical agents.

Further, nanofibers may be used in energy applications such as lithium-ion batteries, photovoltaic cells, membrane fuel cells, and dye-sensitized solar cells and antennas (e.g., high aspect ratio polymer fibers with carbon nanotubes).

Current methods for forming and depositing nanofibers include solution blow spinning, melt spinning, electrospinning, and melt blowing. Solution blow spinning typically involves a first nozzle that supplies a polymer solution (i.e., polymer and solvent) and a second nozzle that supplies a high pressure gas. The polymer solution is forced from the first nozzle and forms a drop or blob. The high pressure gas exiting the second nozzle stretches the polymer solution into a conical shape. When a critical pressure is reached, the polymer/gas mixture travels from the tip of the cone to a target, and as it does, the solvent evaporates leaving polymer fibers, which deposit on the target.

Melt spinning involves drawing down extruded strands of melted polymer to reduce fiber diameter and induce orientation of polymer chains. Melt spinning, however, is restricted to viscoelastic materials that can withstand the stresses developed during the drawing process. Fibers made by melt spinning typically are greater than 2 μm in diameter. A variation of melt spinning that produces nanofibers involves the production of several individual strands of one polymer component within a larger single strand of a second polymer component.

Electrospinning is similar to solution blow spinning in the aspect of forming a cone that stretches to produce polymer fibers. The motive force in electrospinning results from an applied voltage differential between the polymer output device (nozzle) and the target. Accordingly, electrospinning cannot be used on humans without risking harm to the target. Electrospinning has a low fiber production efficiency and is further limited because solvents compatible with the electrospinning process are limited by their dielectric constant.

Melt blowing involves extruding molten polymer through a narrow orifice and into a stream of high velocity hot air. The drag of the hot air on the surface of the molten polymer causes the polymer to elongate into a fiber. However, melt blowing cannot produce fibers with diameters in the same nanoscale size range as in other methods and further is limited to use of thermoplastic polymers.

SUMMARY

A material deposition device comprises a solution supply providing a solution; a gas supply providing a gas; and a discharge device disposed in a center of a discharge orifice plate and a center of a device housing. The discharge device comprises a solution discharge device, comprising an elongated center section defined by a longitudinal axis of the solution discharge device; a supply end of the elongated center section that receives the solution from the solution supply; and a discharge end of the elongated center section comprising a solution discharge port that directs the solution beyond the solution discharge port in a direction along the longitudinal axis of the solution discharge device. The discharge device further comprises a gas discharge device co-axial with the solution discharge device, the gas discharge device comprising a gas insertion cavity that directs the gas into a flow co-axial with the solution. The material deposition device further comprises a discharge device aligner comprising a centering channel that holds the discharge device centered in the housing. The orifice plate comprises a discharge hole centered in the orifice plate, the solution discharge device protruding through the discharge hole past an outer surface of the orifice plate and directing a discharge of the solution, and a first portion of the gas exiting the gas discharge device through the discharge hole, and a plurality of gas discharge orifices disposed parallel to the longitudinal axis, a second portion of the gas exiting the gas discharge device through the orifices, the orifices centered on and spaced away from the discharge hole.

A material deposition device includes a solution supply component, a gas supply component, and a co-axial discharge mechanism. The co-axial discharge mechanism includes a solution discharge mechanism and a gas discharge mechanism co-axial with the solution discharge mechanism. The material deposition device further includes an alignment component that aligns the solution discharge mechanism in a center of the gas discharge mechanism; and an orifice plate with a number of turbulence inducing structures that induce turbulence in gas exiting the gas discharge mechanism.

A method for depositing a material on a target includes supplying a motive gas to a material deposition device, supplying a solution to the device, ejecting the gas and the solution in an approximately co-planar region, and creating a turbulent region for the gas that produces a shearing action on the ejected solution. The shearing action breaks up the solution, and the broken-up solution is accelerated toward the target.

A material deposition device includes a main housing; a gas supply connection disposed in the main housing; a polymer solution connection disposed in the main housing; a gas/solution discharge mechanism, comprising an orifice plate disposed at a discharge end of the main housing, the orifice plate, comprising a center hole defining a central inner surface in the orifice plate; and one or more gas discharge holes spaced away from the center hole, a solution discharge device centered in the main housing by an alignment component and protruding through the center hole creating a gap between an outer circumference of the solution discharge device and the central surface, and the alignment component, comprising a gas discharge device that receives a gas from the gas supply connection, comprising a central channel in the alignment component that funnels the gas toward the orifice plate, the funneled gas exiting the main housing through the center hole and the one or more gas discharge holes, the central channel defining an inner surface.

A material deposition kit includes components that may be used to provide polymer-based fiber layers and other layers in a number of applications. The kit includes a material deposition device that provides co-axial flow of polymer solution and a gas, mixing of the polymer solution and the gas external to a discharge surface of the device so as to break up the polymer solution onto small drops and acceleration of the small drops to a target, and appropriate gas and solution supply tubing, connections, and control valves. In addition, the kit may include a number of different orifice plates and corresponding solution discharge mechanisms. Finally, the kit may include instructions for operating the material deposition device.

A material deposition device comprises means to receive a polymer solution, means for receiving a motive gas, means for providing co-axial flow of the polymer solution and the gas through a centered component of the device, and means to discharge the polymer solution and the gas so as to effectuate break-up of the polymer solution for deposition of fibers on a target surface.

DESCRIPTION OF THE DRAWINGS

The detailed description refers to the following figures in which like numerals refer to like items, and in which:

FIG. 2B shows an exploded perspective view of the device of FIG. 2A;

FIG. 5A illustrates detailed aspects of the device of FIG. 2A;

FIG. 5B illustrates an alternate embodiment of components of the device of FIG. 5A;

FIGS. 6O-6R illustrate an example of material deposition using the device of FIG. 2A in a wound treatment application.

DETAILED DESCRIPTION

Figure 1:
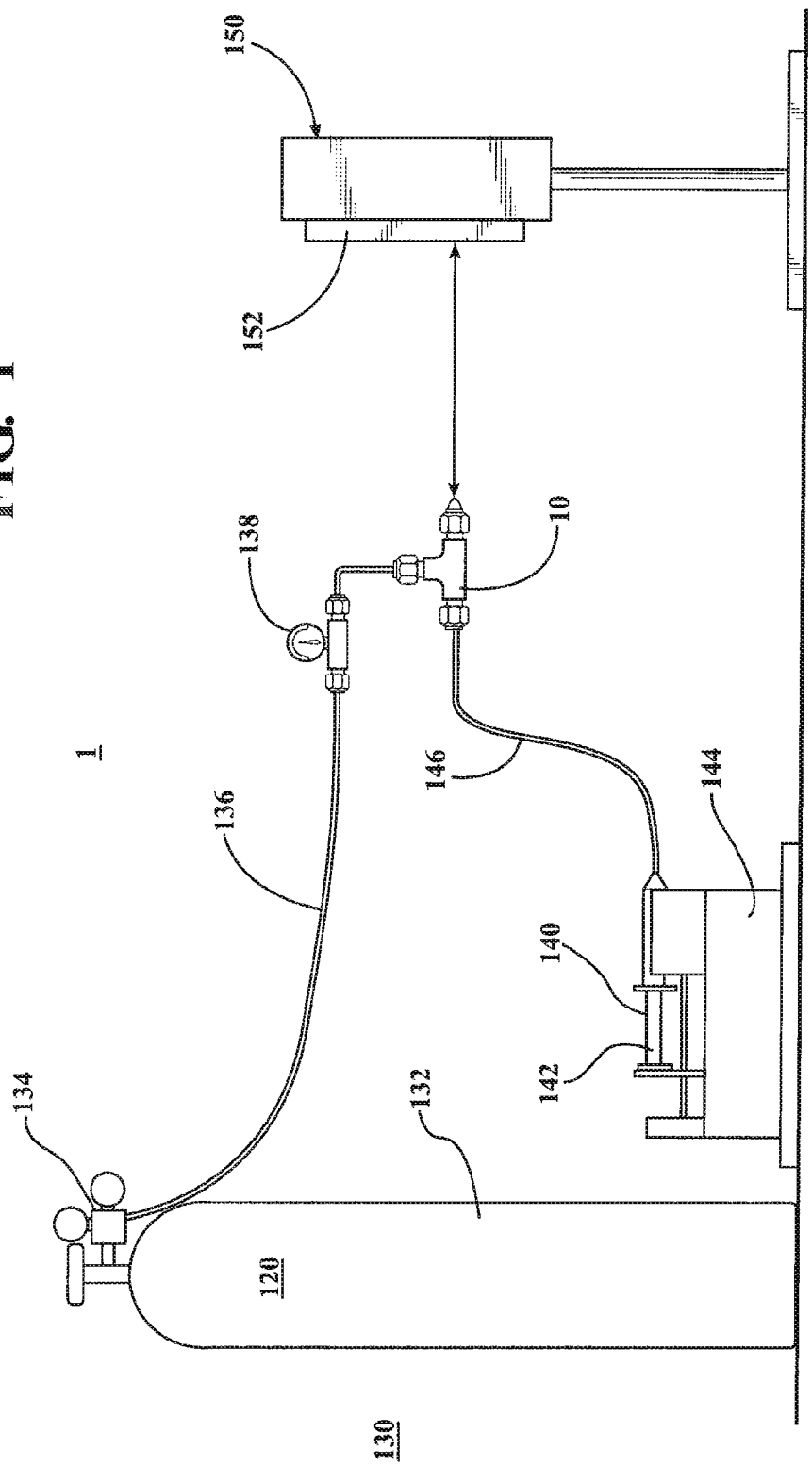
FIG. 1 illustrates an exemplary material deposition system.

Disclosed herein are embodiments of material deposition devices, and corresponding methods of use, that have wide-ranging applications including polymer fiber synthesis, biological cell and hydrogel delivery, direct on-tissue deposition of complex three dimensional scaffolds, and non-medical/dental uses including in electronics, for example. In a specific application, the devices may be used in dental implant/bone graft procedures.

An embodiment of a material deposition device includes a solution supply component, a gas supply component, an orifice plate, and an alignment component, all of which are assembled into a main housing. The material deposition device includes and orifice plate, a solution discharge mechanism, and a gas discharge mechanism. The solution discharge mechanism and the gas discharge mechanism may be co-axial. The orifice plate may include a threaded fastening mechanism that allows for removal of the orifice plate from the main housing of the material deposition device. The alignment component aligns the solution discharge mechanism in a center of the gas discharge mechanism. The solution discharge mechanism may, in an embodiment, include a small-bore tube, or, alternately, a needle. The gas discharge mechanism may include one or more turbulence inducing structures that induce turbulence in gas exiting the gas discharge mechanism.

The specific gas, polymer solution, gas flow rate, polymer flow rate, and pressures may depend on a specific application. In applications such as those shown in FIGS. 6A-6L, the material deposition device may receive a low flow rate gas, such as $CO_2$, $N_2O$, $N_2$, and other gases, supplied at a flow rate of less than 10 ml/h, and a solution, such as a polymer solution, supplied at a volumetric flow rate having a range of approximately 5 to 40 ml/h and preferably approximately 20 ml/h. For optimum material deposition, the solution flow rate may be chosen based on the fiber synthesis rate. The fiber synthesis rate, in turn, may depend on the orifice plate configuration as well as the configuration of the solution discharge mechanism (e.g., the inner diameter and outer diameter of the small-bore tube or needle and the amount of protrusion of the tube/needle beyond the orifice plate).

In an embodiment, the gas discharge occurs in a first plane and, by virtue of the solution discharge mechanism protruding beyond the outer surface of the orifice plate, the solution discharge occurs in a second plane spaced beyond the first plane. This multi-planar arrangement enhances break-up of the exiting solution into small droplets that more readily evaporate. In another embodiment, the solution discharge and the gas discharge occur in approximately a same plane, wherein turbulence of the discharged gas induces shearing in the discharged solution.

The herein disclosed devices and methods provide significant advantages over current systems and methods employed for nanofiber deposition. For example, using the herein disclosed material deposition device embodiments, polymer fibers are deposited more effectively than is possible with current systems. The herein disclosed devices, and corresponding methods, use, for example, a polymer solution (at an entangled, semi-diluted concentration), ejected at a velocity A, which is mixed in an ambient environment with a gas at a velocity B, and the polymer/gas mixture then is directed toward a target. The material deposition device creates one or more turbulent flow regimes, which effectively break up the polymer fiber solution into small droplets. The small polymer solution droplets evaporate during flight to the target. The polymer fibers then are effectively deposited on a target, including on a living organism and without the potential for harm to the organism. More specifically, the disclosed devices and methods provide for material (e.g., Food and Drug Agency (FDA)—approved polymers) deposition at high volume without excessive force (i.e., at low pressure) along with low toxicity solvents, and without use of electrical current, thereby obviating damage to target tissue or risk to a patient. Thus, the herein disclosed devices and methods are well-suited for medical/dental applications that involve human subjects. One such application is to provide bone grafts to support dental implants, as discussed herein in more detail.

A similar material deposition process may be used with other biological materials such as cells and hydrogels, for example. However, the flow dynamics of the gas and the biological materials may require adjustment in order to provide a specific, desired outcome. For example, the process may be used to attract cells, direct their development, and induce healing and proper tissue regeneration.

The herein described devices and methods allow for the production of micro and nanofibers with polymer fiber diameters similar to those of other material deposition processes. In an embodiment, a material deposition device includes a polymer solution discharge mechanism (in an embodiment, a needle) and orifice plate arrangement through which a polymer solution is injected into a gas stream. The gas may be provided by a compressed gas source equipped with a pressure regulator, a device to hold the polymer solution for injection into the needle, a pump to control the injection rate of the polymer solution, and a target to receive the polymer fibers. The target may be stationary and positioned at a fixed working distance from the needle. Alternately, the target may be stationary but the distance between the target and the material deposition device may vary.

The needle may be centered in a needle aligner. The needle aligner may be supplied with a motive gas, such as $CO_2$, at the same time that the polymer solution is supplied to the needle. The gas exits the needle aligner in coordination with discharge of the polymer solution from the needle. The gas then exits the material deposition device through the orifice plate, and the design and placement of orifices in the plate creates or enhances a turbulent flow regime, which causes the exiting polymer solution to break into small droplets. An aspect of the needle/needle aligner is the ability to adjust how far the needle protrudes beyond the planar face of the orifice plate. In an embodiment, the needle may be adjusted, for example, to protrude 0.1 to 10 times the inner diameter of the needle. The amount of protrusion may be chosen based on the specific solution being ejected from the needle. The design of the material deposition device provides one or more turbulent flow regimes at optimum locations, both internal and external to the material deposition device) to cause shearing of the polymer solution as or after it is ejected from the needle.

A solvent may be used that allows delivery of the material or substance through the needle and that is sufficiently volatile so as to evaporate before the solution reaches the target. The solvent may be used for dissolving or suspending the material or the substance to be deposited. Solvents useful for dissolving or suspending a material or a substance depend on the material or substance. The solvent selected preferably has a low evaporation temperature. Solvent selection also depends on the application. For example, in a bio-application, the solvent should be non-toxic or minimally toxic. However, in an electronics application, solvent toxicity normally is not a consideration. Acetone is an example of such a solvent.

Synthetic polymers that may be used by the herein disclosed material deposition devices include biodegradable and non-biodegradable polymers. The selected polymers may have a molecular weight of more than 40 kDA and should be in an entangled, semi-diluted regime. Such polymers include, for example, polymethyl methacrylate (PMMA), polystyrene (PS), and polyurethanes, or any other similar synthetic polymers that may be developed that are biologically compatible. The following polymers have been tested with this invention: (PS, taken from the bottoms of tissue culture polystyrene dishes, catalog number 430599, Corning), polydesaminotyrosyl-tyrosine ethyl ester carbonate (pDTEc, made as described (10)), poly-D,L-lactic acid (PDLLA, SurModics Pharmaceuticals) and poly-□-caprolactone (PCL, Sigma-Aldrich).

Natural polymers normally do not form fibers. However natural polymers, if heated and/or when used in colloidal suspensions with synthetic polymers (e.g., a suspension of chitosan and PLA), also may be used with the herein disclosed material deposition device. Examples of such natural polymers include amino acids, peptides, denatured peptides such as gelatin from polypeptides, proteins, carbohydrates, lipids, nucleic acids, glycoproteins, minerals, lipoproteins, glycolipids, glycosaminoglycans, and proteoglycans.

Fibers made from the polymer solutions mentioned above are readily formed into nonwoven sheets using a generally stationary target. Thus, nonwoven webs are easily and safely collectable on a variety of targets including living tissue.

The concentration of polymer in the polymer solution may range from 1% to 60%, and preferably 5% to 20% in solution. Increasing the polymer concentration may increase the fiber diameter and conversely, fiber diameters may be smaller when using lower polymer concentrations.

The material deposition devices also may be used to deposit other biological materials and pharmaceutical agents. Pharmaceutical agents may be organic or inorganic and may be in a solid, semisolid, liquid, or gas phase. Molecules may be present in combinations or mixtures with other molecules, and may be in solution, suspension, or any other form. Examples of molecules that may be used include any molecules that can cause a cellular or physiological response. Any combination of molecules can be used, as well as agonists or antagonists of these molecules.

Pharmaceutical agents also include any therapeutic molecule including any pharmaceutical substance or drug.

When used for depositing cells, the material deposition device may be operated to provide a solution having a cell concentration of more than 10 k/250 uL of media but less than 200 k/250 uL of media, and preferably at a deposition rate of between 60-120 ml/h.

FIG. 1 illustrates an embodiment of a material deposition system. In FIG. 1, system 1 includes material deposition device 10, gas supply 130, polymer supply device 140 and target 150. Embodiments of the material deposition device 10 are described with respect to FIG. 2A and following. The gas supply 130 provides a gas 120 (see FIG. 5A) from, for example, gas cylinder 132 through pressure regulator 134, gas supply tube 136 and control valve 138. Polymer supply device 140, in an embodiment, includes a polymer solution supply 142 and pump device 144, which is coupled to material deposition device 10 through tube 146. Target 150, in an embodiment, includes substrate 152, which receives material from the material deposition device 10. Note, however, that the target 150 may take many forms, including on a human patient. For example, the system 1 may provide deposition of material to form a bone graft to support a dental implant. As disclosed herein, the supply of material to the target 150 may be at low pressure and high volumetric flow rate. Furthermore, the material may be supplied at a high surface area to volume ratio.

FIG. 2A is an exploded view showing component parts of an embodiment of material deposition device 10. In FIG. 2A, material deposition device 10 includes cylindrical main housing 20, internal drum/needle aligner 30, needle assembly 40, needle stopper 50, and diffusion/orifice plate 60. The main housing 20 includes central cavity 22 into which is inserted the internal drum/needle aligner 30. The cavity 22 may be machined to provide a tight tolerance fit of the internal drum/needle aligner 30. Alternately, or in addition, the needle aligner 30 and main housing 20 may be provided with an o-ring or wall seal (not shown). The main housing 20 includes gas port 24, which, in an embodiment, is a threaded opening into which a gas supply tube 136 (see FIG. 1) is fitted to supply a gas, as described below.

A front, or diffusion, end 26 of the main housing 20 may be recessed and provided with threaded holes to attach diffusion/orifice plate 60. An aft, or material insertion, end 28 is machined and adapted to receive needle stopper 50. The aft end 28 is further machined to provide a close tolerance fit insertion hole/centering channel 29 into which the needle assembly 40 is inserted.

The internal drum/needle aligner 30 is a machined cylinder having a necked-down gas insertion cavity 32 that, when the needle aligner 30 is assembled into the main housing 20, aligns with the gas port 24. The necked-down gas insertion cavity 32 includes a number of holes 34 arranged radially around its circumference. The holes 34 allow gas supplied by the gas supply tube to enter a hollow central region, or channel, 36 of the needle aligner 30 and move toward the front end 26 of the main housing 20. A front end 39 of the central region 36 is further machined to form a structure (in the example embodiment of FIG. 2A, a conical structure) 37 that allows gases provided to the gas port 24 and through holes 34 to exit the forward end 26 of the main housing 20 through orifices 64 and other openings machined into, or otherwise provided in, the orifice plate 60, as described below. The needle aligner 30 further includes a central cavity 38 through which a needle 42 of the needle assembly 40 passes and which forms a close tolerance fit with the needle 42.

The needle assembly 40 is formed with a hollow, elongated needle 42 that connects with a material supply adapter 44. An inner diameter of the needle 42 may be sized to allow efficient/rapid material deposition at a low gas flow rate so as to provide good operational safety. The inner diameter also may be sized to limit clogging during use. In an embodiment, the needle 42 may have an inner diameter in the range of 0.6 mm to 1.0 mm and preferably an inner diameter of 0.818 mm (or G 22). The volumetric flow rate of the gas may be less than 10 ml/h. In this embodiment, the outer diameter of the needle 42 may be sized to provide a close tolerance fit with the opening 29 of the housing 20 and the central cavity 38 of the needle aligner 30. As shown, the opening 29 aligns with the central cavity 38 to center the needle assembly 40 in the main housing 20.

Other needles may be used with the needle assembly 40. For example, other needles with a same outer diameter but with larger or smaller inner diameters may be used with the needle assembly 40. This arrangement allows quick swapping of needles during a material deposition process.

As can be seen, the needle assembly 40 and needle aligner 30 when assembled into the main housing 20 form a co-axial solution discharge/gas discharge device.

The needle stopper 50 is a flat plate that is fixedly attached to a flat surface of the housing 20. The needle stopper 50, when installed, prevents movement of the needle assembly 40. The needle stopper 50 may be affixed to the housing 20 so as to allow the needle 42 to protrude a desired distance past the surface defining the front end 26 of the main housing 20 and the diffusion/orifice plate 60. The actual amount of protrusion may depend on the polymer type and concentration used for a specific application. The arrangement of the needle stopper 50 allows for rapid changing of needles and rapid positioning of the needle 42 during a material deposition process.

Figure 2A:
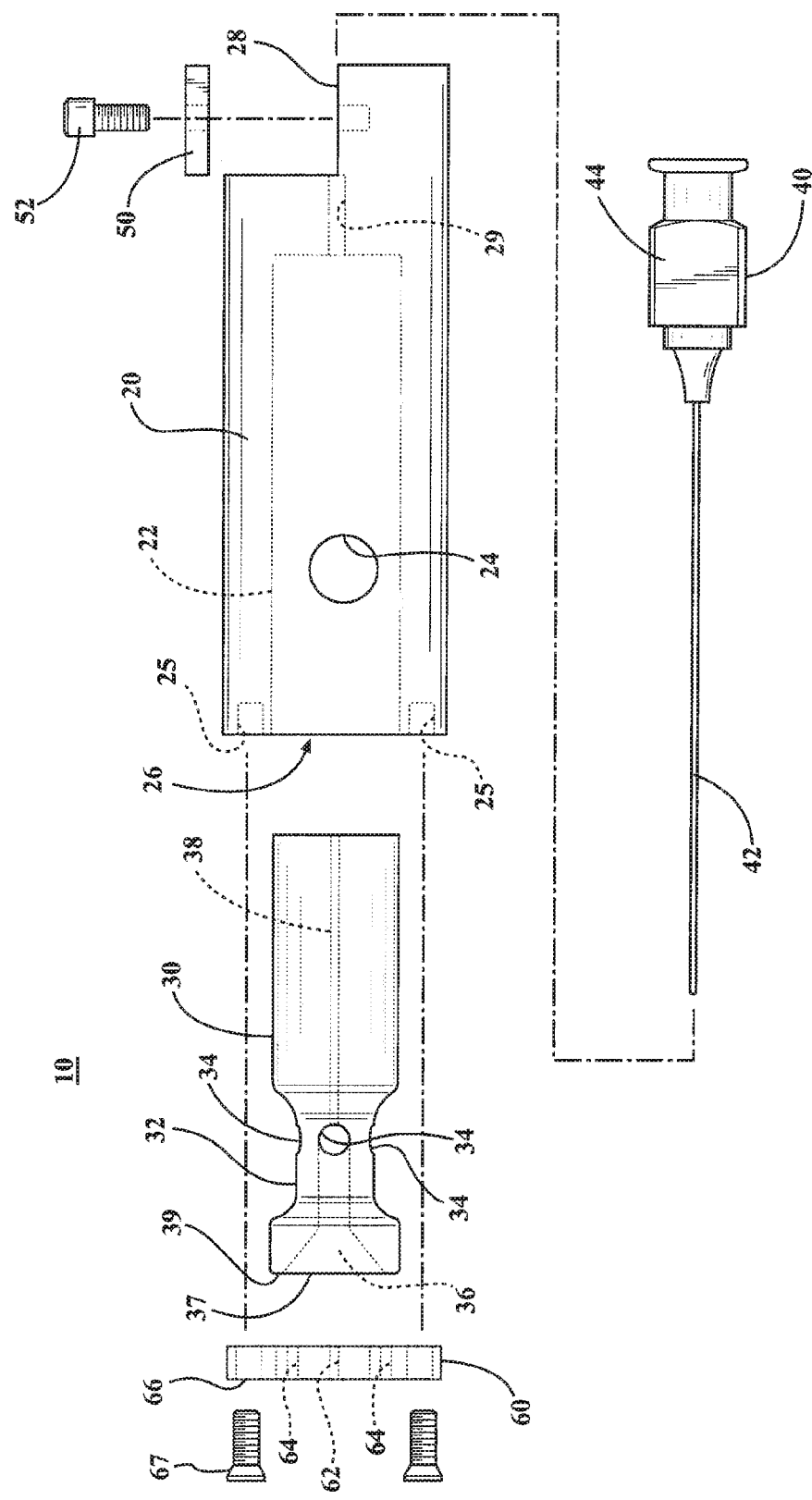
FIG. 2A is an exploded view showing component parts of an embodiment of a material deposition device.

The diffusion/orifice plate 60 may be machined to have a circular shape and may be fixedly attached to the housing 20 using mounting screws 67 passing through holes 66 machined into the plate 60. The plate 60 includes a central opening 62 through which passes the needle 42. Note that the illustrated diameter of the central opening 62 is for illustration only, and a larger or smaller diameter opening may be used. Because of its centered alignment ensured by the needle aligner 30, the needle 42 is concentrically aligned in the central opening 62. As shown in the embodiment of FIG. 2A, the central opening 62 provides a passage along the outer surface of needle 42 for gas 120 to exit the material deposition device 10. The advantages of this configuration are described herein, including with respect to FIG. 5A. In another embodiment, the central opening 62 may be machined to provide a close tolerance fit with the needle 42.

In a specific application, the material to be deposited begins as an entangled, semi-diluted polymer solution that is ejected from the needle 42 and broken up (and, e.g., may be atomized and/or extruded) and dispersed by the gas exiting the orifices 64 and central opening 62.

The co-axial needle/needle aligner components carry pressurized gas to make use of Bernoulli's principle in which changes in pressure are converted into kinetic energy. Facilitated by the orifice plate design, the exiting gas induces shearing at the gas/solution interface, which exists a short distance from the outer surface 61 (see FIG. 3B) of the orifice plate 60. The shearing effectively breaks up the polymer solution, enhancing its travel to the target, and ensuring a generally even distribution of polymer fibers on the target. While in flight, solvent in the polymer solution rapidly evaporates, leaving behind polymer fibers that accumulate on the collector or target.

The above-described co-axial design of gas and solution discharge mechanisms provides better control over shearing forces and, consequently, fiber formation on the target. Furthermore, the design is scalable for many different applications. See, for example, FIGS. 6M-6R and their accompanying descriptions below. Finally, the co-axial design provides reproducible results in terms of fiber formation among similar applications.

The material deposition device 10 and certain of its components may be manufactured from stainless steel. In an embodiment, the needle 42 may be manufactured from glass while other components are manufactured from stainless steel. Other materials, such as aluminum, also may be used.

FIG. 2B shows an isometric, exploded view of the material deposition device 10 of FIG. 2A. As can be seen, the aft end 28 of the housing 20 includes passage 29 in which the needle 42 is placed, and which serves to center the needle 42 in the housing 20 and aligner 30. FIG. 2B also illustrates surface 27, which receives the needle stopper 50.

Figure 3A:
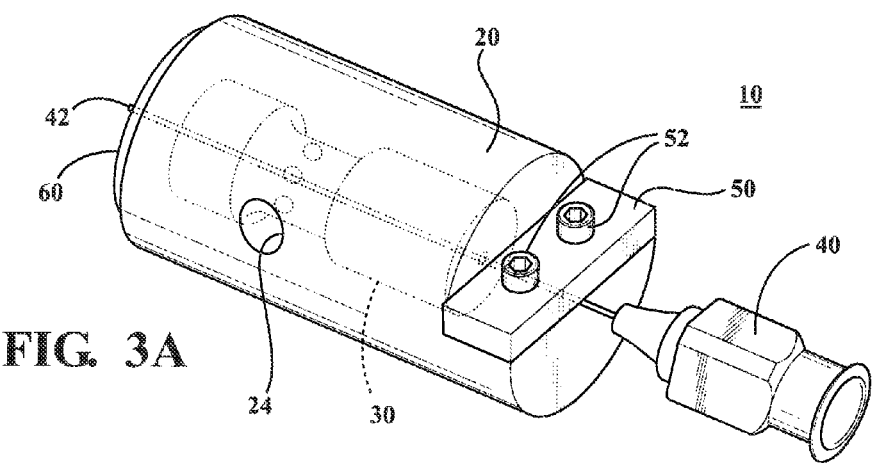
FIGS. 3A and 3B are isometric views of the assembled device of FIG. 2A.

FIG. 3A is a rear isometric view of the assembled material deposition device 10 of FIG. 2A.

Figure 3B:
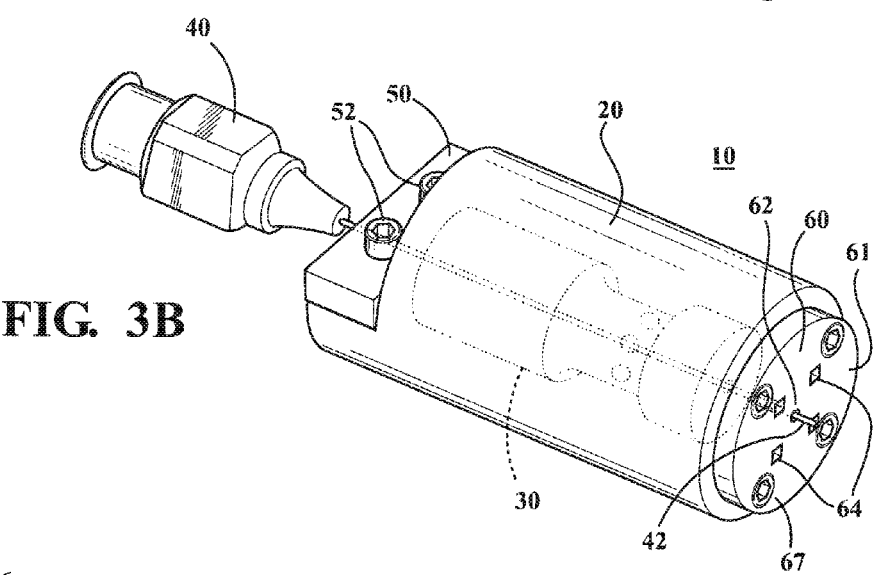

FIG. 3B is an isometric front view of the assembled material deposition device 10 of FIG. 2A. As can be seen, the needle 42 protrudes from center hole 62 of front surface 61 of diffusion/orifice plate 60. In an embodiment, the needle 42 may protrude 1 to 4 mm beyond the orifice plate 60, and preferably 2-3 mm. The needle 42 is held in this protruding position by the stopper 50. The orifice plate 60 is fastened to the main housing 20 with fasteners 67. The orifice plate 60 can be easily removed and replaced.

Figure 4:
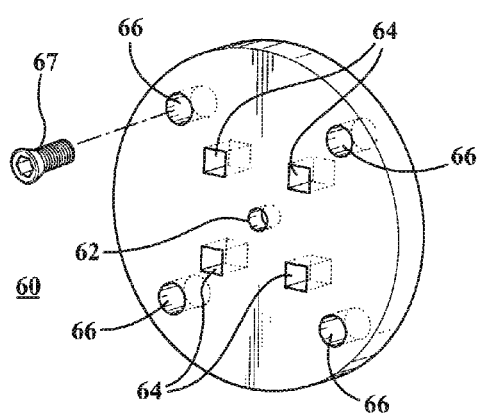
FIG. 4 illustrates an embodiment of a diffusion/orifice plate component of the device of FIG. 2A.

FIG. 4 illustrates an embodiment of a diffusion/orifice plate 60 of the material deposition device 10 of FIG. 2A. In FIG. 4, orifice plate 60 is machined to have a number of assembly holes 66 through which fasteners 67 are passed to secure the plate 60 to the main housing 20. Orifice plate 60 further includes central opening 62 through which needle 42 of needle assembly 40 is passed. Orifice plate 60 still further includes a number of gas orifices 64 through which the motive gas exits the main housing 20. The location, shape, and number of orifices 64 may be provided so as to induce turbulent flow in the exiting gases (i.e., cause an enhanced turbulent flow region to exist at the exit of the needle assembly 40). In an embodiment, the orifices 64 are provided so as to form gas passages that are parallel to the longitudinal axis of the main housing 20 and the needle 42. In an embodiment, the orifices 64 are square in cross-section. Other cross-sectional shapes, including circular, triangular, and other shapes are possible. The orifices 64 may be machined to have an expanding shape from the rear surface of the plate 60 to the front surface of the plate 60. At their exits, the orifices 64 may be formed with sharp edges to further induce turbulent flow of the exiting gas. In an embodiment, the orifices 64 may be formed in a fractal pattern.

In addition to gas flow through the orifices 64, the orifice plate 60 provides gas flow through the central opening 62 through which the needle 42 protrudes, and along the outer circumference of the needle 42. The gas exiting through the central opening 62 impacts the polymer solution exiting the needle 42 adding to the shearing forces generated by the gas exiting the orifices 64. See FIG. 5A.

In another embodiment, the orifice plate 60 uses means other than assembly screws or fasteners 70 to attach to the main housing 20. For example, the orifice plate 60 may employ a bayonet-type connector or simply may screw onto the main housing 20. In one specific embodiment, the main housing 20 may be formed with male threads and the orifice plate 60 with corresponding female threads. These attachment schemes allow for rapid replacement of the orifice plate 60 during a material deposition process.

FIG. 5A illustrates components of the material deposition device of FIG. 2A in more detail. In FIG. 5A, liquid polymer solution 110 is supplied through needle 42 under pressure from polymer injector 140 (see FIG. 1). Simultaneously, gas 120 (for example, $CO_2$) is supplied from gas source 130 (FIG. 1) through port 24, enters central region 36 of needle aligner 30, and flows toward the discharge end of needle 42.

The discharge end of the needle 42 protrudes a distance X beyond the outer surface of orifice plate 60. The amount of protrusion may depend on the solution being ejected, the application or target parameters, and the gas used with the device. The amount of protrusion X may vary from 0 mm (i.e., no protrusion) to 4 mm or more. For many applications, the protrusion X may be in the range of 1 mm to 3 mm.

As can be seen in FIG. 5A, the liquid polymer solution 110, upon exiting the needle 42, assumes, initially, a roughly spherical shape—that is, a blob or drop. At the same time, gas 120 exits the internal drum 30 through central opening 62 in orifice plate 60 and travels approximately along the outer circumference of needle 42 past outer surface 61 of the orifice plate 60. The gas 120 exiting the central opening 62 impinges the exiting polymer solution 110, causing the blob to begin breaking up into small droplets 111. This provides a first turbulent flow. Simultaneously, the gas 120 entering conical structure 37, exiting the internal drum 30, and then entering and exiting orifices 64 of orifice plate 60, transitions to a turbulent flow regime, thereby providing a second turbulent flow, which eventually merges with the first turbulent flow. The size, shape, and placement of the orifices 64 in the orifice 60 ensure that the combined turbulent flow is approximately symmetrical around the central opening 62. The net result of the turbulent flowing gas 120 impinging the expanding (and breaking-up) liquid polymer solution 110 is that the liquid polymer solution 110 breaks apart into a number of small droplets 111, which move toward and ultimately deposit fibers on the target substrate 150. Note also, that with the arrangement of components of the device 10 as shown in FIG. 5A, the turbulent flow region is enhanced at the point of discharge of solution 110 from needle 42. More specifically, the exiting gas 120 begins to transition to turbulent flow in the region 37, and the turbulence increases at a first plane defined by the surface 61 of the orifice plate 60 because of the number and shape of the orifices 64 and the gas exiting the central opening 62. Thus, the gas discharge and corresponding more fully-developed turbulent gas flow, and the solution discharge are approximately co-planar. This arrangement further facilitates the break up and dispersion of the solution 110 into droplets 111.

The droplets 111 comprise the liquid polymer solution, but the enhanced shearing action of the turbulent flow of the gas 120 has caused the ejected liquid polymer solution 110 to beak-up into many finer droplets 111, thereby increasing the total surface area of the liquid polymer solution and correspondingly accelerating evaporation of the solvent portion of the liquid polymer solution 110. When the solvent evaporates, polymer fibers are left, and the turbulent gas stream helps to carry the fibers to the target substrate 152, where they deposit a nonwoven fiber layer 112.

As noted, the needle 42 may have an inner diameter of 0.818 mm, the gas 130 may be $CO_2$ at a gas pressure that results is a volumetric flow rate of the gas 130 of less than 10 ml/h, and the liquid polymer solution 110 may be supplied at a volumetric flow rate in the range of approximately 5 to 40 ml/h and preferably approximately 20 ml/h. Finally, a ratio of the inner diameter and outer diameter of the needle may be on the order of 0.4 to 0.7, and preferably approximately 0.58, and the inner diameter may be in the range of 0.6 to 1.0 mm. These factors mean the material deposition device 10 may deliver materials and fibers without clogging the needle 42 while quickly and safely depositing a high quality nonwoven fiber layer 112.

FIG. 5B shows an embodiment of the internal drum/needle aligner 30 having additional features to facilitate break-up of the polymer solution 110. In FIG. 5B, the hollow central region 36 is formed with spiral groves 31 which create some amount of turbulence in the gas 120 as the gas 120 travels toward the orifice plate 60.

FIGS. 6A-6L illustrate examples of material deposition using the material deposition devices disclosed herein. FIGS. 6A-6F illustrate material deposition for site healing for teeth with intrabony or furcation lesions, and FIGS. 6G-6L illustrate material deposition for bone graft/bone regeneration.

FIG. 6A is a cross sectional side view of a section of a patient's jaw showing tooth 200 in bone 210 and gingiva 220. As can be seen, intrabony lesion 230 has formed. FIG. 6B is a top view of the jaw section of FIG. 2A.

FIG. 6C is a side view of the jaw section of FIG. 6A showing deposition of a tissue formation enhancing layer 240 in the area of the lesion 230. FIG. 6D is a top view corresponding to FIG. 6C.

FIG. 6E is a side view and FIG. 6F is a top view of the jaw section of FIGS. 6C and 6D, respectively, after membrane 250 has been deposited over layer 240.

The layer 240 and membrane 250 may be deposited by a material deposition device as described herein. An example of such a device, intended for dental applications, is described below and illustrated in FIG. 6M.

Figure 6A:
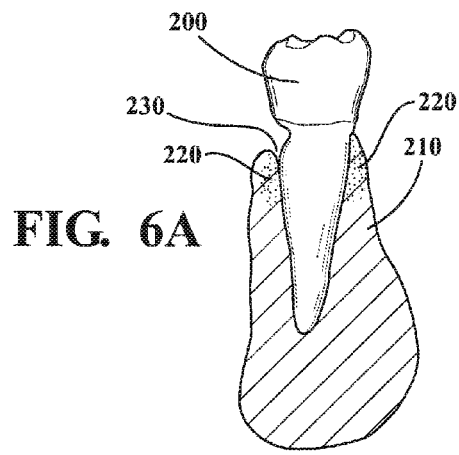
FIGS. 6A-6L illustrate examples of material deposition using the device of FIG. 2A.
Figure 6B:
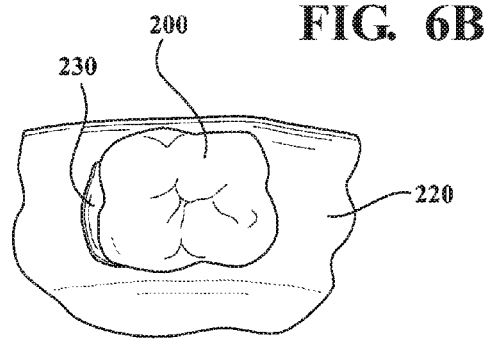
Figure 6C:
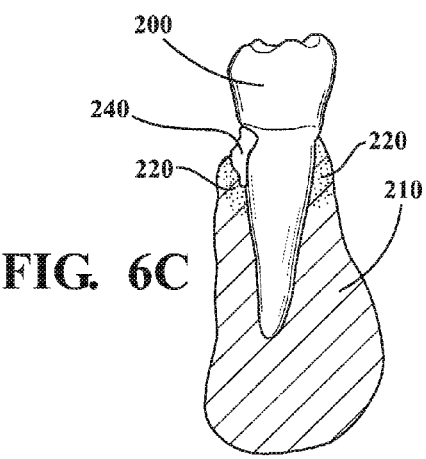
Figure 6D:
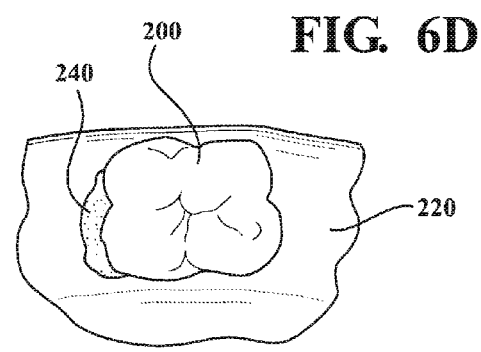
Figure 6E:
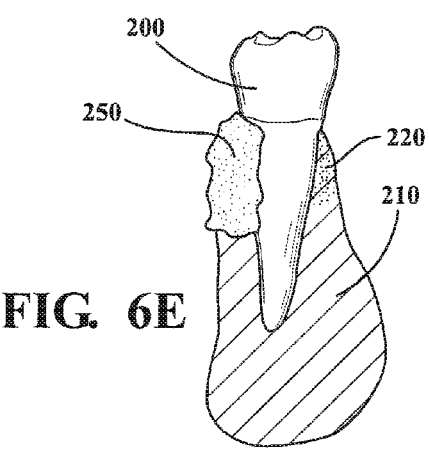
Figure 6F:
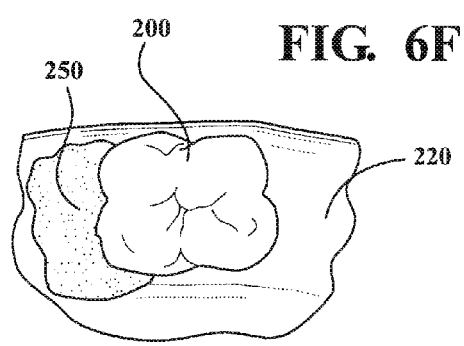
Figure 6G:
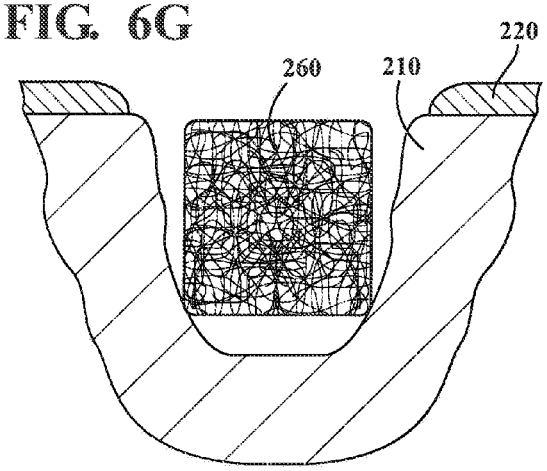
Figure 6H:
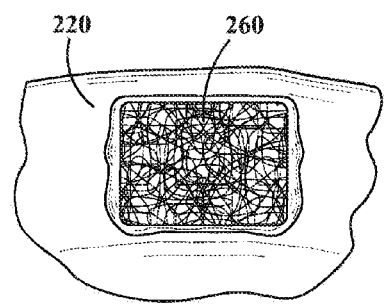

FIG. 6G is a side view and FIG. 6H is a corresponding top view of a patient's jaw bone 210 and gingiva 220 showing deposited bone cell material 260. Once the bone cell material 260 is healed in the site, the patient may receive a dental implant anchored in the bone cell material 260.

Figure 6I:
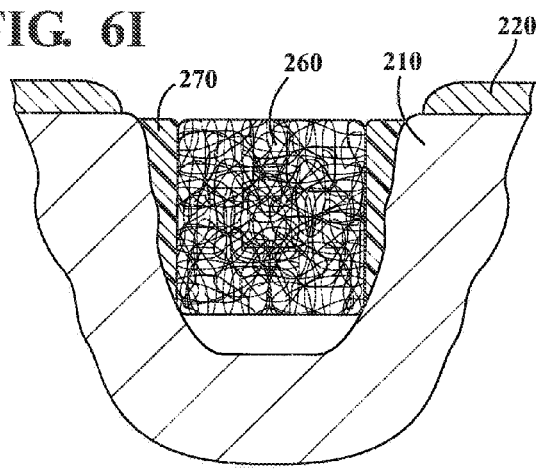
Figure 6J:
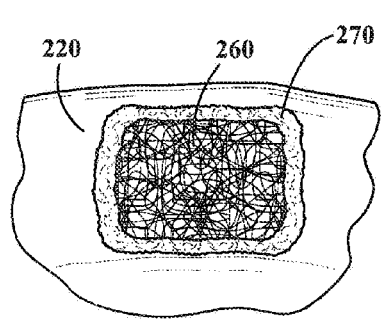

FIG. 6I is a side view and FIG. 6J is a corresponding top view of the patient's jaw bone 210 and gingiva 220 after deposition of a thin inner layer 270 of polymer nanofibers has been deposited around the bone cell material 260. The nanofibers in the layer 270 are loaded with biomolecules to promote bone cell adhesion and differentiation.

Figure 6K:
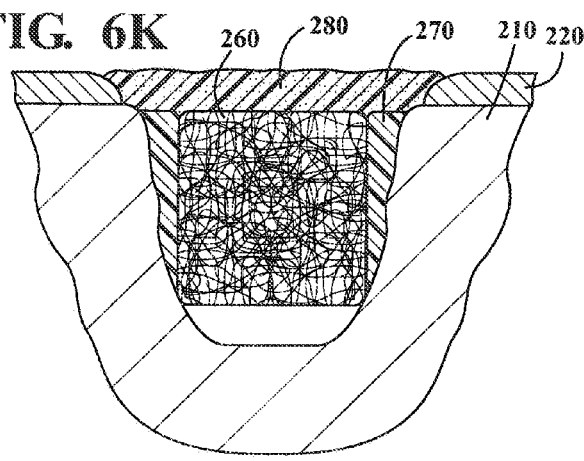
Figure 6L:
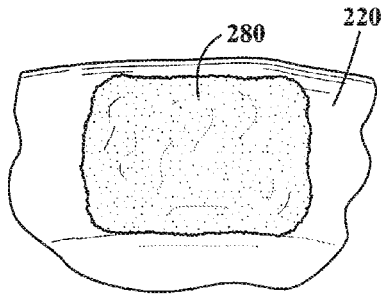

FIG. 6K is a side view and FIG. 6L is a corresponding top view of the patient's jaw bone 210 and gingiva 220 after deposition of a thin outer layer 280 of polymer fibers, loaded with antimicrobial molecules to prevent cell penetration.

Figure 6M:
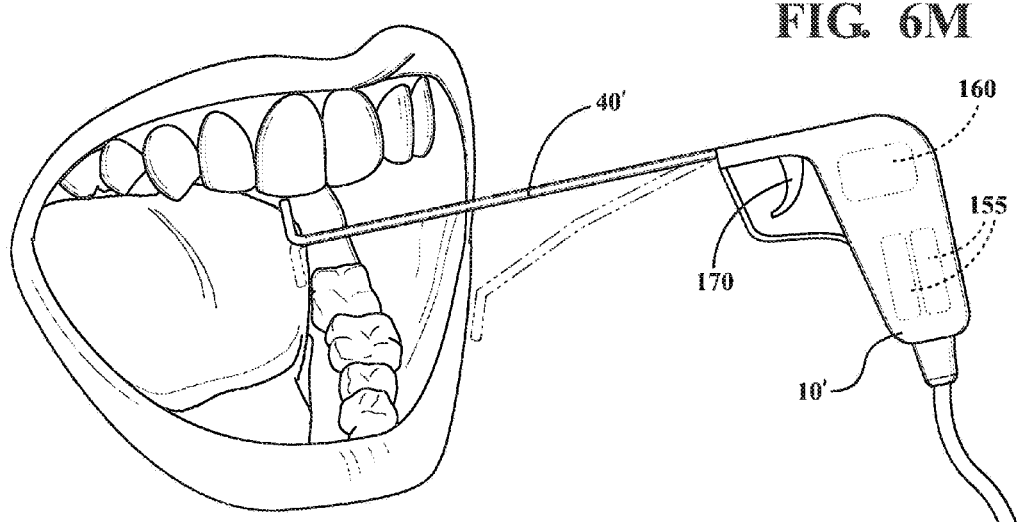
FIG. 6M illustrates a specific embodiment of a material deposition device used in a dental application.

FIG. 6M illustrates a specific embodiment of a material deposition device used in dental applications such as those of FIGS. 6A-6L. In FIG. 6M, material deposition device 10' is illustrated in a position to deposit material in a patient's mouth. A motive gas such as $N_2$ or $CO_2$ is supplied through an attached hose. A polymer is provided in one or more replaceable cartridges 155 in a handle of the device 10'. The device 10' includes needle assembly 40', which as shown is an elongated tube. The needle assembly 40' uses the same or similar co-axial structure as that illustrated in FIG. 2A. That is, the polymer solution flows through an inner tube (not shown in FIG. 6M). The polymer solution may be ejected by use of a pump 160 housed in the handle of the device 10', where the pump is activated by operation of the illustrated trigger 170.

The ejection end of the needle assembly 40' may use the same or similar orifice plate design as shown in FIG. 2A. As shown by the dotted lines, the needle assembly 40' is flexible, and can be moved or bent to reach a selected site within the patient's mouth. Thus, the material deposition device 10' may be used in a variety of dental applications such as lesion healing and dental implant applications.

Figure 6N:
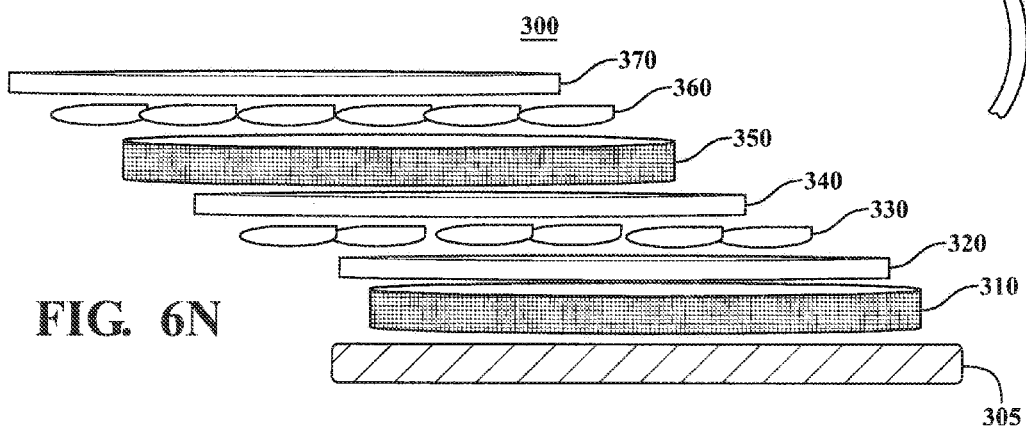
FIG. 6N illustrates an example of layers of materials that may be deposited in a specific application using the device of FIG. 2A.

FIG. 6N illustrates an example of layers of materials deposited in a specific application such as for wound healing and tissue regeneration. FIG. 6N shows direct on-tissue generation 300 in which three basic materials are interchangeably deposited: live cells, proteins, and polymer fibers. The fibers may contain growth factor bio-molecules that are released in a time-dependent manner. Certain of the layers containing polymer nanofibers are biodegradable, and the degradation rates of the fibers are tunable to suit a specific application.

In FIG. 6N, deposition surface 305 receives layers of material deposited by a material deposition device as described herein. The surface may be gum tissue, bone, skin (i.e., a wound site), or part of an organ such as the pancreas, for example. In the illustrated example, surface 305 is bone material. The first deposited layer 310 may be a first nanofiber matrix that promotes osteogenesis. Layer 320 may be a protein that facilitates osteogenesis. Layer 330 may be a cellular layer (for example bone stromal cells). Layer 340 may be a second protein layer. Layer 350 may be a second nanofiber matrix to promote angiogenesis. Next, layer 360 contains cellular material such as endothelial cells. Finally, layer 370 contains proteins to facilitate angiogenesis.

Each of the layers shown in FIG. 6N may be deposited using material deposition device as disclosed herein. Each type of layer may be more efficiently deposited by varying the supply gas, solvent, pressure, material deposition rate, and other factors. The herein described devices may be used to deposit these different types of layers by simply adjusting the operating parameters of the device (temperature, pressure, flow rate) and/or by changing the needle (smaller or larger inner/outer diameter needle).

FIGS. 6O-6R illustrate another application of the material deposition device 10. These figures illustrate deposition of fiber layers over a (simulated) hand wound. FIG. 6O illustrates hand 400 with wound 410. FIGS. 6P-6R illustrate fiber film 420 as it is applied to the wound 410. Use of the material deposition device 10 in the application illustrated in FIGS. 6O-6R resulted in the wound 410 being covered in about 15 seconds.

The above illustrated components may be incorporated into a kit. The kit may be designed to satisfy a number of applications. For example, a kit may comprise the components shown in FIG. 2A in addition to gas and solution supply tubing, connections, and control valves. In addition, the kit may include a number of different orifice plates 60 and corresponding solution discharge mechanisms 40. Finally, the kit may include instructions for operating the material deposition device 10.

Figure 7:
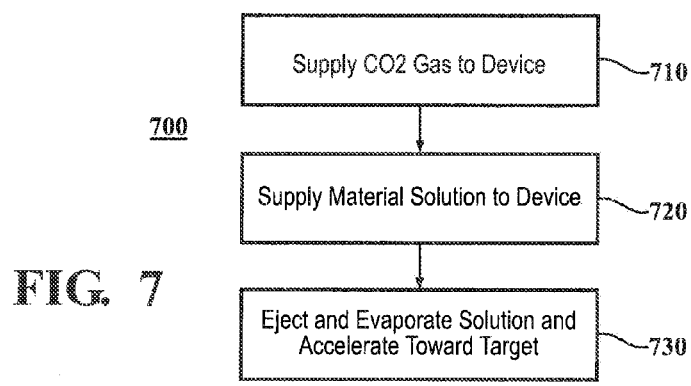
FIG. 7 is a flowchart illustrating steps in a process for depositing material from the device of FIG. 2A onto a target.

FIG. 7 is a flowchart illustrating steps in a process for depositing material from the material deposition device 10 of FIG. 2A onto a target. In an embodiment, the target is a living human receiving a bone graft to support a dental implant, and the material to be deposited includes cellular material extracted from the human in solution with a bio-degradable polymer. The material may include agents designed to induce growth of cells. The bio-degradable fiber may degrade at a rate commensurate with cell growth. The material may be applied in layers to generate the bone graft.

In FIG. 7, method 700 begins in block 710 with supply of a motive gas, such as $CO_2$, to a material deposition device such as the material deposition device 10 of FIG. 2A. Simultaneously or nearly simultaneously, in block 720, a solution is supplied to the device 10. The amount of polymer solution fed to the device 10 may be determined based on the gas energy necessary to break up the polymer solution. In an embodiment, the polymer solution may be heated, which may lower the gas energy required to break up the polymer. Next, in block 730, the gas and solution are ejected in an approximately co-planar region at the discharge end of the device 10; and a turbulent region for the gas beginning at the co-planar region is created. The turbulence creates a shearing action on the ejected solution that serves to atomize the solution. The forces generated by the supplied gas and solution cause the atomized solution to accelerate toward the target.

I claim:

1. A material deposition device, comprising:
   a solution supply providing a solution;
   a gas supply providing a gas;
   a discharge device disposed in a center of a discharge orifice plate and a center of a device housing, the discharge device comprising:
      a solution discharge device, comprising:
         an elongated center section defined by a longitudinal axis of the solution discharge device;
         a supply end of the elongated center section that receives the solution from the solution supply; and
         a discharge end of the elongated center section comprising a solution discharge port that directs the solution beyond the solution discharge port in a direction along the longitudinal axis of the solution discharge device, and a gas discharge device co-axial with the solution discharge device, the gas discharge device comprising a gas cavity that directs the gas into a flow co-axial with the solution, a discharge device aligner comprising a centering channel that holds the solution discharge device centered in the housing and the orifice plate, the centering channel defining an inner surface, the centering channels, comprising:

a first portion of the inner surface, the first portion comprising one or more spiral grooves formed on the inner surface at a first portion of the inner surface of the central channel, and a second portion adjacent to and downstream of the first portion, the second portion comprising an expanding chamber adjacent the orifice plate; and the orifice plate comprising:

an opening centered in the orifice plate, the discharge device protruding through the opening past an outer surface of the orifice plate and directing a discharge of the solution, and a first portion of the gas exiting the gas discharge device through the opening, and a plurality of gas discharge orifices disposed parallel to the longitudinal axis, a second portion of the gas exiting the gas discharge device through the orifices, the orifices centered on and spaced away from the opening.

2. The material deposition device of claim 1, wherein the solution discharge device comprises an inner diameter in the range of 0.6 to 1.0 mm and preferably approximately 0.818 mm.

3. The material deposition device of claim 1, wherein each of the orifices comprises a plurality of edges that impart turbulence to the gas exiting the orifice.

4. The material deposition device of claim 1, wherein the gas discharge device aligner further comprises a gas insertion cavity that aligns with the gas port to direct a flow of the gas in a direction along the longitudinal axis.

5. The material deposition device of claim 1, further comprising a solution discharge device stop plate that clamps the solution discharge device in the housing to lock an amount of protrusion of the solution discharge device beyond the orifice plate.

6. The material deposition device of claim 1, wherein the solution comprises a liquid polymer in a solvent.

7. The material deposition device of claim 6, wherein the turbulent exiting gas disperses the solution enabling evaporation of the solvent and formation of polymer fibers.

8. The material deposition device of claim 6, wherein the solution further comprises biological material that adheres to the polymer fibers.

9. The material deposition device of claim 8, wherein the biological material comprises human cellular material.

10. A material deposition device, comprising:

a main housing;

a gas supply connection disposed in the main housing;

a polymer solution connection disposed in the main housing;

a gas/solution discharge mechanism, comprising:

an orifice plate disposed at a discharge end of the main housing, the orifice plate, comprising:

a center hole defining a central inner surface in the orifice plate; and one or more gas discharge holes spaced away from the center hole, a solution discharge device centered in the main housing by an alignment component and protruding through the center hole creating a gap between an outer circumference of the solution discharge device and the central surface, and the alignment component, comprising:

a gas discharge device that receives a gas from the gas supply connection, comprising:

a central channel in the alignment component that funnels the gas toward the orifice plate, the funneled gas exiting the main housing through the center hole and the one or more gas discharge holes, the central channel defining an inner surface, the central channel, comprising a first portion of the inner surface of the inner channel, the first portion comprising one or more spiral grooves formed on the inner surface at the first portion of the inner surface of the central channel; and a second portion adjacent to and downstream of the first portion, the second portion comprising an expanding chamber adjacent the orifice plate.

* * * * *